United States Patent [19]

Purdy et al.

[11] 4,267,837
[45] May 19, 1981

[54] BLOOD COLLECTION MONITORING DEVICE AND METHOD

[75] Inventors: Robert W. Purdy, Sunnyvale, Calif.; Don A. Arneson, Elgin, Ill.

[73] Assignee: SBR Lab Inc., Elgin, Ill.

[21] Appl. No.: 79,487

[22] Filed: Sep. 27, 1979

[51] Int. Cl.³ .............................................. A61F 5/44
[52] U.S. Cl. .................................. 128/275; 128/214 E
[58] Field of Search ............... 128/214 E, 272.1, 275, 128/214 R, 213 R, 213 A

[56] References Cited

U.S. PATENT DOCUMENTS

| | | | |
|---|---|---|---|
| 3,557,789 | 1/1971 | Poitras | 128/275 |
| 3,848,603 | 11/1974 | Throner | 128/275 |
| 4,095,658 | 6/1978 | Kendall et al. | 128/214 E |
| 4,137,915 | 2/1979 | Kamen | 128/214 E |

FOREIGN PATENT DOCUMENTS 2508735 9/1976 Fed. Rep. of Germany ... 128/214 E

Primary Examiner—Robert W. Michell
Assistant Examiner—T. J. Wallen
Attorney, Agent, or Firm—James W. Potthast

[57] ABSTRACT

This invention is directed to apparatus and a method for monitoring the collection of blood from a donor so as to minimize trauma to the blood so collected. The system closely monitors the rate of collection of blood and regulates the rate of mixing of anticoagulant therewith so as to maintain a substantially constant ratio of anticoagulant to blood throughout the collection process. The system also includes built-in warning devices for indicating when the collection process is not proceeding according to a prescribed pattern.

6 Claims, 11 Drawing Figures

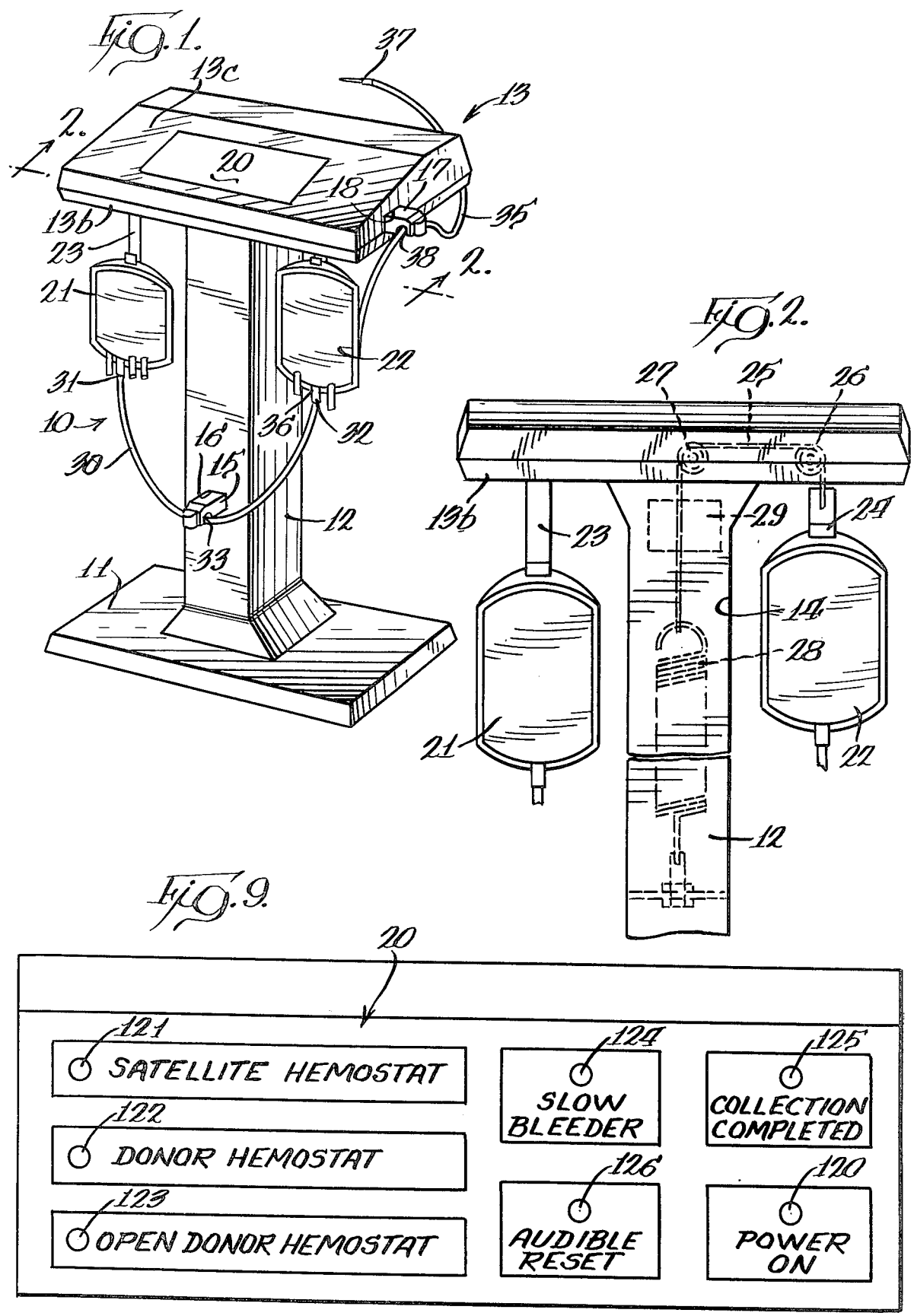

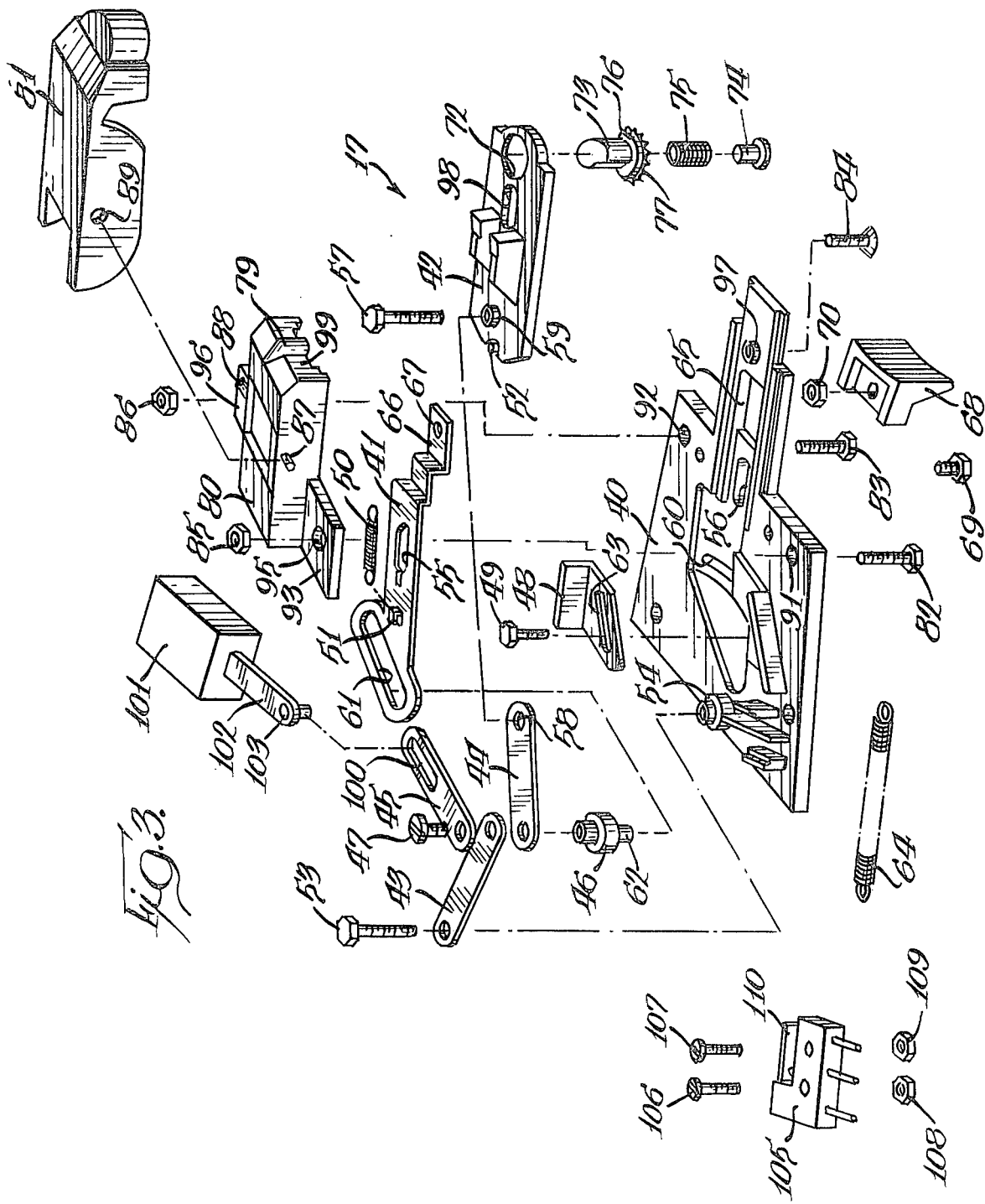

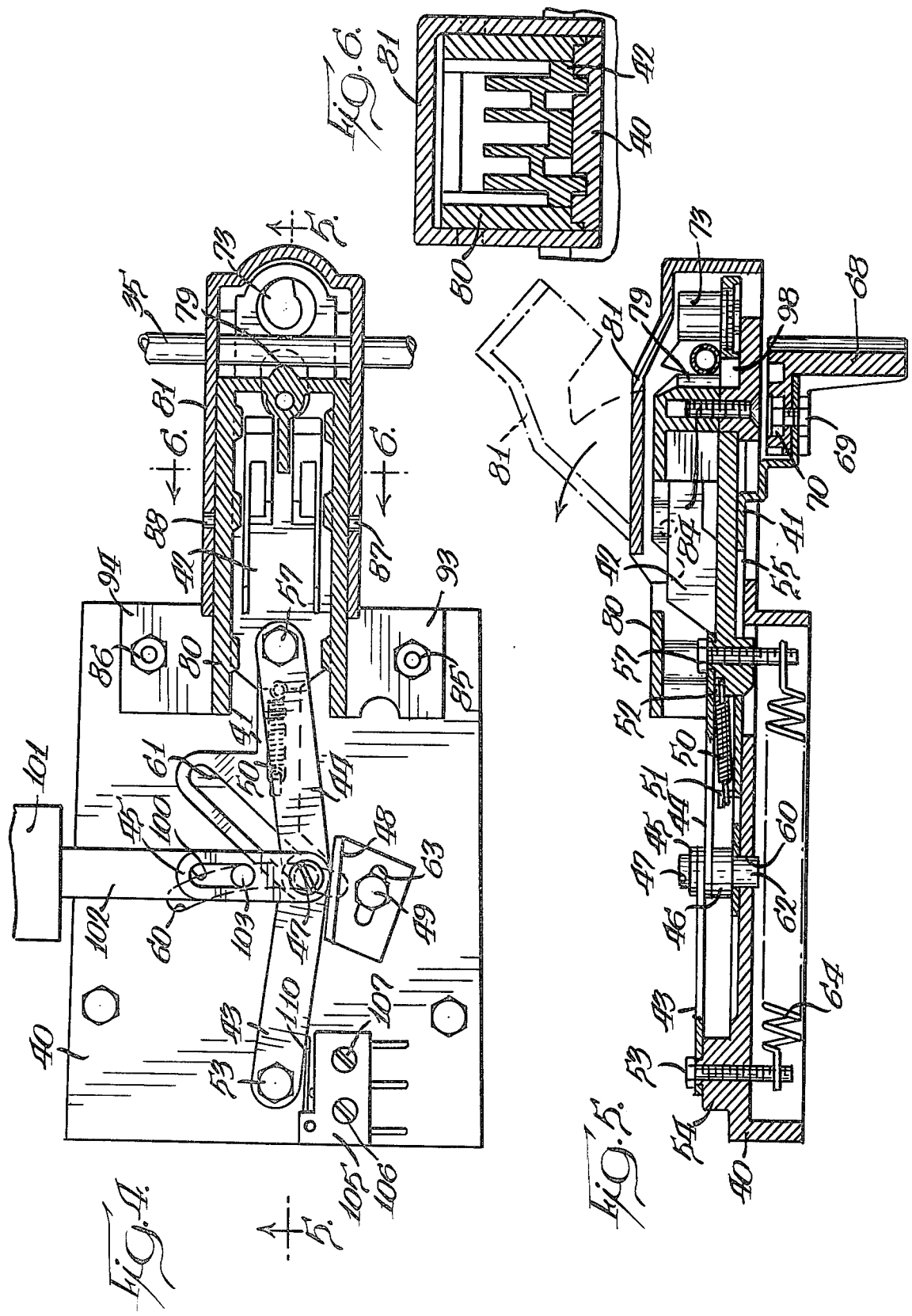

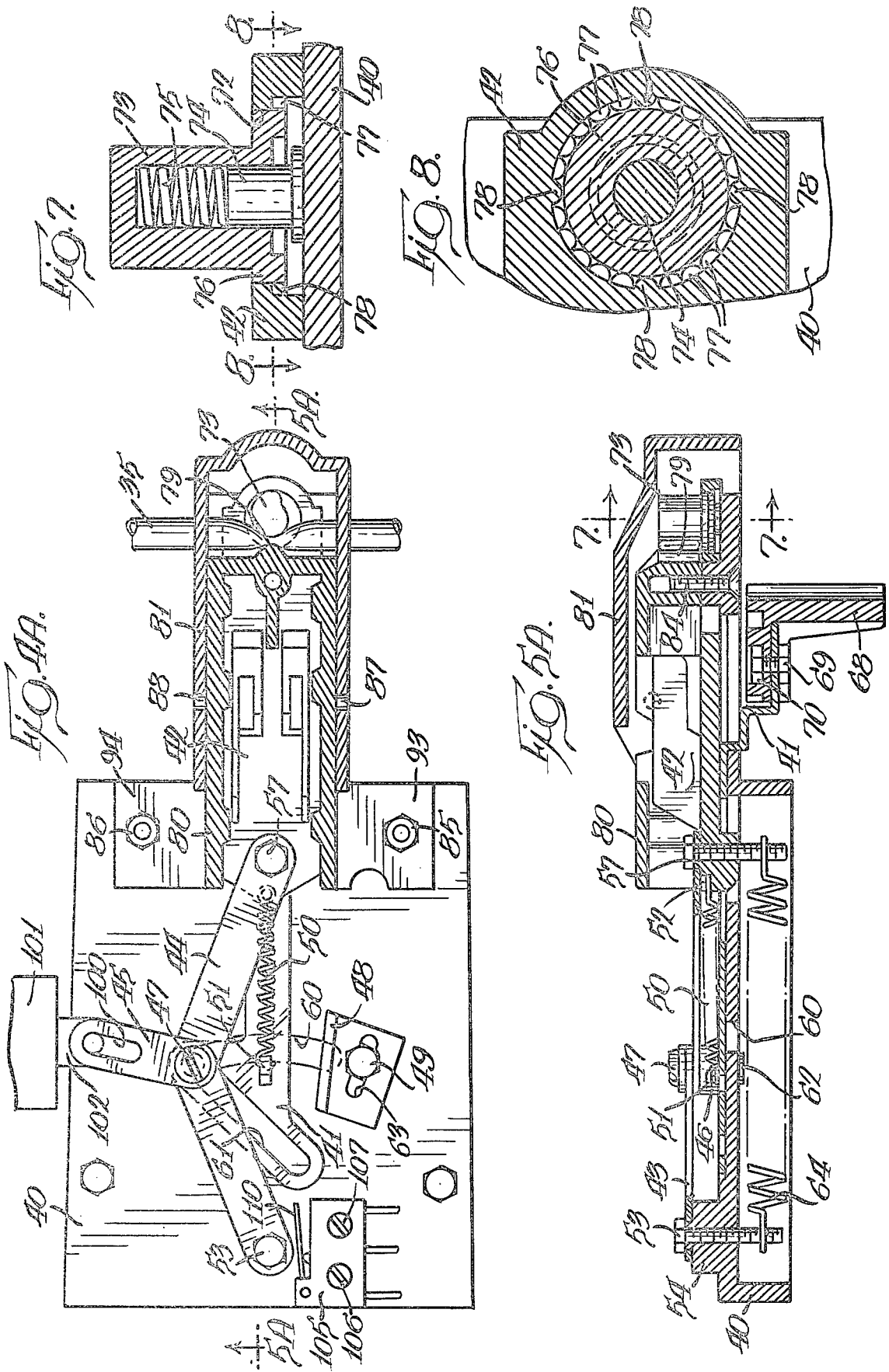

BLOOD COLLECTION MONITORING DEVICE AND METHOD

CROSS REFERENCE TO RELATED APPLICATIONS

This application constitutes an improvement to an earlier filed application entitled "Biological/Pharmaceutical Fluid Collection and Mixing System and Method" in the names of John P. McCue and Mogens L. Bramson filed Aug. 1, 1978, Ser. No. 928,411, and assigned to the same assignee.

BACKGROUND OF THE INVENTION

1. Field of the Invention

This invention relates generally to the field of surgery and more particularly to hemostatic instruments and devices for monitoring the collection of blood from donors. The apparatus described herein is also called a "Standard Blood Ratiometer".

2. Description of the Prior Art

The problems associated with trauma to blood cells induced or caused by the blood collection process has been described by John G. Gibson et al. in his article entitled "The Influence of Extra-Cellular Factors Involved in the Collection of Blood in ACD on Maintenance of Red Cell Viability During Refrigerated Storage" (*The American Journal of Clinical Pathology*, August 1956, 855-). A recognition and partial solution to the problem has also been suggested in the earlier application of McCue and Bramson referred to above.

Conventional blood collection bags currently available consist of a donor blood transfer tube attached to a main collection bag in which anticoagulant is placed during manufacture. Also connected to the main collection bag by similar but separate tubing are one or more satellite bags similar in construction, but smaller than the main collection bag. These satellite bags normally contain no liquid. The satellite bags are isolated from the main bag by a tube diaphragm which is opened when use of the satellite bag is desired.

Conventional blood collecting procedures call for receiving approximately one pint of blood (450 ml) in a plastic bag containing 63-75 ml of anticoagulant. Nearly all of the conventional anticoagulants such as ACD, CPD and CPD-Adenine are stongly acidic, having a pH in the range of 4.95 to 5.63. In addition, these anticoagulants contain the complexing agent, citrate, that strips red blood cells of essential cations, e.g., $Ca^{+2}$ and $Mg^{+2}$. The initial exposure of blood collected into the bag containing the anticoagulant causes trauma to a high percentage of the early collected cells because of the relatively hostile environment presented by the high proportion of anticoagulant. As the proportion of blood to anticoagulant increases, this tendency diminishes, but the damaged early cells still remain within the collection bag.

If the blood were alternatively collected in a bag that was dry and the anticoagulant added subsequently, the contact of the red blood cells with the dry plastic could also cause coagulation or clotting or otherwise induce trauma to the cells.

The conventional blood collecting procedures have also been found to have an adverse effect on the stability of blood coagulation factors (particularly Factors V and VIII) in plasma and have also had an adverse effect on the preservation of platelet function. The literature ("Blood Collection: Stability of Factors V and VIII in Plasma, V. L. Kermon, et al—Experimental Hematology, Vol. 7, No. 6, 1979, pp. 68) indicates that Factors V and VIII rapidly lose the capacity to function after being withdrawn from the circulatory system. In 0.02 M Oxalate at 22° C. approximately 50% of Factor V activity is lost within two hours. In citrate phosphate dextrose (CPD) 50% of Factor V activity has been reported to be lost in 48 hours at 4° C.

In a separate study ("Blood Collection: Preservation of Platelet Function", D. J. Stevens, et al—Experimental Hematology, Vol. 7, No. 6, 1979, pp. 65) the loss of platelet effectiveness and function was examined with respect to the lesion of collection and storage of the blood. It was observed that platelets from blood collected into CPD by the standard technique could not be induced to release ADP, as measured by in vitro biphasic aggregation responses to exogenous ADP or epinephrine.

SUMMARY OF THE INVENTION

The primary object of the present invention is to provide a method and apparatus for collecting blood from a donor in a controlled manner so as to minimize trauma to the blood so collected.

It is a more particular object to provide apparatus for monitoring the collection of blood from the donor comprising two plastic bags, one of which contains a liquid anticoagulant and the other of which serves as a receiving bag for the collected blood. The collection bag is connected to a resilient means which permits the collection bag to descend vertically due to the weight of blood collected. The anticoagulant bag is interconnected by a suitable tube and meters anticoagulant into the collected blood at a controlled rate so as to maintain a substantially constant ratio of blood to anticoagulant.

It is an additional object to provide an apparatus and method for collecting blood in a manner that allows the blood and the anticoagulant to flow freely together at a fixed rate during the entire collection process. This improved method and apparatus removes the initial shock of the high concentration of anticoagulant.

It is still another object to provide a method and apparatus of the type described effective to improve platelet functional capabilities as well as erythrocytes and leukocyte functions. This improved method and apparatus is a simple, rapid, safe, non-invasive procedure for anticoagulation during collection of whole blood.

The apparatus also includes two hemostats, one for interrupting the flow of blood from the donor into a collection bag, and the second for interrupting the flow of anticoagulant into the collection bag. The apparatus also includes sensing and alarm means for detecting and warning of any abnormalities encountered in the collection process.

It is a more particular object to provide apparatus for monitoring and control of the collection of blood from a donor into a main collection bag which has been wetted with anticoagulant prior to the introduction of blood, thus precluding undesired coagulation or clotting.

BRIEF DESCRIPTION OF THE DRAWINGS

FIG. 1 is a perspective view of the improved apparatus for use in the present invention;

FIG. 2 is a front view, partially in section, of the blood collection stand of FIG. 1;

FIG. 3 is a perspective exploded view of the blood donor hemostat of FIG. 1;

FIG. 4 is an enlarged top view showing the internal structure of the blood collection hemostat of FIG. 1 in an open position;

FIG. 4A is a view showing the hemostat of FIG. 4 in a closed position;

FIG. 5 is a cross-sectional view taken on line 5—5 of FIG. 4;

FIG. 5A is a cross-sectional view taken on line 5A—5A of FIG. 4A;

FIG. 6 is a cross-sectional view taken on line 6—6 of FIG. 4;

FIG. 7 is an enlarged cross-sectional view of the restriction cam taken on line 7—7 of FIG. 5A;

FIG. 8 is a top sectional view taken on line 8—8 of FIG. 7; and

FIG. 9 is a top view of the control panel for the apparatus of FIG. 1.

DETAILED DESCRIPTION OF THE PREFERRED EMBODIMENT

The blood collection metering apparatus of the present invention, otherwise designated as the Standard Blood Ratiometer (SBR) is contained within or mounted upon a stand designated generally by the numeral 10. The stand 10 is a unitary structure generally in the form of a letter I and comprises a base 11, a vertical upright column or post 12 mounted on top of the base 11, and a horizontal two-piece console 13 mounted on top of the column 12. The column 12 is generally U-shaped in cross-section and is covered with a removable backplate 12a. The console 13 comprises a base 13b and a console cover 13c. The column 12, with backplate 12a in place, is generally rectangular in cross-section and has a hollow interior cavity 14. The structural components 11, 12 and 13 of stand 12 are preferably constructed of structural foam plastic, but might be constructed of metal, wood, plastic or combinations thereof.

A first manually operated hemostat 15 is mounted within the column 12 and projects through an opening 16 in the front face of column 12. A second electromagnetically actuated hemostat 17 is mounted on the console base 13b and projects horizontally through an opening 18 in one end of the console cover 13c. A monitoring and control panel 20 is mounted in the top of console cover 13c for easy viewing.

A replaceable blood collection bag assembly is attached to and is adapted to be used in conjunction with the stand 10 and comprises at least one satellite bag 21 and a blood collection bag 22, both of which are mounted on the underside of the console base 13b. The bag 21 is attached to a relatively fixed hook 23 mounted on the underside of the base 13b. This hook 23, while fixed in operation, may be adjustable up and down within a limited range of motion to accommodate different sized bags, and different relative distances between fluid levels in bags 21 and 22. The collection bag 22 is hung on a movable hook 24 which in turn is attached to a longitudinally movable tape or ribbon 25. The tape 25 extends over pulleys 26 and 27 mounted within the console 13 and extends downward through the interior 14 of column 12 where it is attached to one end of a tension spring 28. The other end of spring 28 is attached to the base of the hemostat 15. A photocell detector 29 is mounted within the cavity 14 near the top of column 12 and is adapted to detect relative positions of the tape 25. The tape 25 may have one or more holes formed therein for detecting the relative position of the tape and the photocell detector 29 may be adjustable up and down within a limited range to calibrate the tape for its desired range of motion.

The satellite bag 21 and the collection bag 22 are interconnected by an anticoagulant delivery tube 30 connected between a nipple 31 in the bottom of bag 21 and a nipple 32 in the bottom of bag 22. The tube 30 is intercepted by the hemostat 15 at the point 33. The hemostat 15 is adapted to cut off the flow of anticoagulant from a satellite bag 21 to the collection bag 22 until such flow is required. A blood collection tube 35 is connected to a nipple 36 in the bottom of bag 22. The free end of tube 35 carriers a needle 37 adapted for insertion into the vein of the donor. The blood collection tube 35 is intercepted by the hemostat 17 at a point 38 and is adapted to cut off the flow of blood from the donor into the blood bag 22 when required.

Referring now to FIGS. 3, 4 and 5 there are illustrated details of structure of the hemostat 17 of FIG. 1. FIG. 3 is an exploded view in order to more clearly identify the individual parts and FIGS. 4 and 5 are views showing the parts completely assembled. The hemostat 17 as a whole comprises a base 40, a horizontally movable push bar 41, a dynamic clamp beam 42, link arms 43 and 44, and a solenoid link 45. The links 43, 44 and 45 are joined together at a common point by a link connector pin 46 and machine screw 47. An adjustable over-center stop 48 is attached to the base 40 by means of a screw 49. A spring 50 is attached at one end to a tab 51 formed on the push bar 41 and the other end of spring 50 is attached to a pin 52 formed on the dynamic beam 42. The link 43 is attached at one end to a pivot pin 53 which is screwed into the base 40 at a boss 54. The push bar 41 is formed with a longitudinal slot 55 which is adapted to overlie a slot 56 formed in the base 40. A screw 57 extends through a hole 58 formed in one end of link 44 and is threaded through a boss 59 formed in the dynamic beam 42 and extends downward through the slots 55 and 56. The base 40 is formed with an arcuate slot 60, and the push bar 41 is formed with an angular slot 61. The pin 46 has a downwardly extending stem 62 which extends through slots 61 and 60 in the assembled condition. The over-center stop 48 is formed with a slot 63 to permit adjustment of the position of the stop with respect to the base 40. A spring 64 is attached at one end to the screw 53 and at the other end to the screw 57. The base 40 is also formed with a rectangular opening 65 in the portion of the base that extends through the opening 16. The push bar 41 is formed with a "stepped" external end 66 having a hole 67. The stepped end 66 extends through the slot 65 and has attached thereto a push bar handle 68 by means of a screw 69 and nut 70. The dynamic beam 42 is formed with a circular aperture 72 through which extends an adjustable cam 73. The cam 73 is attached to the beam 42 by means of a plug 74. A bias spring 75 is contained within the cam 73 under compression against the plug 74. The cam 73 has a circular base 76 having a plurality of serrated teeth 77 formed on its perimeter.

A static clamp beam 80 and its tiltable cover 81 are attached to the base 40 by means of screws 82, 83 and 84 and nuts 85 and 86. The cover 81 is attached to the static beam 80 by means of two horizontally extending bosses 87 and 88 which extend through holes 89 and 90 formed in the cover 81. The machine screws 82 and 83 extend upward through holes 91 and 92 formed in the base 40.

The static beam 80 is formed with horizontal flanges 93 and 94 which in turn are formed with holes 95 and 96 which match the holes 91 and 92 and are secured in place by the nuts 85 and 86 attached to the screws 82 and 83 respectively. The base 40 is formed with a boss at 97, and the dynamic beam 42 is formed with a slot 98. The screw 84 extends upward through the boss 97 and through the slot 98 and attaches to the static beam 80 at the point 99. The solenoid link 45 is attached at one end, by means of pin 46 and screw 47, to the links 43 and 44 and is also formed with a slot 100 for attachment to a solenoid 101. The solenoid 101 has an armature 102 carrying a pin 103 for connection through the slot 100 to the link 45.

Referring to FIG. 5, the hemostat 17 is shown with the cover 81 lifted to an alternate position (in dotted line) for allowing insertion of the blood donor tube 35. The tube 35 is inserted in place between the cam 73 and a raised nose 79 formed on the outermost end of the static beam 80. The cam 73 is adjustable for accommodating different diameters of plastic tubes 35. This adjustment is accomplished by pushing the cam 73 downward against the force of the spring 75 and turning the cam 73 to the desired clearance to accommodate the particular diameter of tube 35. Pushing the cam 73 downward disengages the teeth 77 from a plurality of raised splines 78 formed in the aperture 72. Once the tubing 35 is engaged between the cam 73 and nose 79, the cover 81 is returned to its normal horizontal position.

The hemostat 17 can be actuated manually or electromagnetically by means of the solenoid 101. The internal structure of the hemostat 15 is substantially identical to the structure of hemostat 17 except that it is operated only manually. The relative position of the hemostat 17 in either a totally open or totally closed position is detected by means of a microswitch arrangement 105 which is attached to the base 40 by means of screws 106 and 107 and nuts 108 and 109. The switch 105 has a leaf or arm 110 which is adapted to be contacted by the link 43 and indicates either a totally open condition as shown in FIG. 4 or a totally closed condition as shown in FIG. 4A.

Referring now to FIG. 9, there is illustrated a diagram of the control panel 20 for the apparatus 10. The control panel 20 comprises a number of indicating lights 120, 121, 122, 123, 124 and 125, and an audible reset switch 126. A power switch (not shown) for the unit 10 may be located beneath the base of the console 13b and the indicator light 120 shows when the power is on. The light 121 is designated as the satellite hemostat indicator and shows when the satellite 15 is either open or closed, the light being on when the hemostat is closed. The light 122 is designated as the donor hemostat indicator and is on when the hemostat 17 is closed. The light 123 is designated as the open donor hemostat indicator. This light 124 goes on after a predetermined period of time and is accompanied by an audible beep to advise the operator that a predetermined amount of anticoagulant has flowed from the satellite bag 21 into the blood collection bag 22. This in effect tells the operator that it is now time to open the donor hemostat 17. The light 124 is designated as a "slow bleeder" indicator. This light 124 comes on if a predetermined amount or weight of blood is not collected within a one-minute time span. The indicator 124 also comes on after ten minutes, or other predetermined length of time, in the event the collection is not completed during some prescribed time period. The light 125 is designated as a collection completed light and comes on when the collection procedure has been totally completed. The audible reset 126 is a manually actuated switch which cuts off the audible signal due to a slow bleeder condition, which is sometimes encountered.

A description of the procedure and the operation of the Ratiometer 10 will now be described for a complete cycle:

The technician or operator begins by turning on the power switch (not shown), the on condition being indicated by the light 120 on the control panel 20. In the event the anticoagulant is contained initially within the blood collection bag 22, the anticoagulant is transferred through the tube 30 to the satellite bag 21 and the bag 21 is hung on the hook 23. The tube 30 is placed in the restriction slot 33 of hemostat 15 and the manual handle corresponding to handle 68 is actuated to close off the flow of anticoagulant through tube 30. Closing the hemostat 15 turns on the light 121 to indicate that the satellite hemostat 15 is closed.

The technician then hangs the main collection bag 22 on the hook 24 and places the donor tube 35 in the restriction slot 38 of hemostat 17. The handle 68 is then pushed inwardly clamping the tube 35 between the cam 73 and nose 79. Depending on the diameter of the tube 35 so inserted, it may be necessary to first calibrate the cam 73 to accommodate the particular diameter tube. This is accomplished by lifting the cover 81 and pressing the cam 73 downward against the force of the spring 75 so as to disengage the teeth 77 from the splines 78. The cam 73 is then turned to the desired dimension and released re-engaging the teeth 77 with the spline 78. Closing off the tube 35 by means of the handle 68 also is effective to actuate the switch 105 thereby turning on the donor hemostat light 122.

The technician then inserts the needle 37 in to a vein of a donor to initiate flow of blood into tube 35.

The technician then manually opens the satellite hemostat 15 by pulling on the handle corresponding to handle 68. The satellite hemostat light 121 goes out and an electrical timing circuit (not shown) is initiated by a switch corresponding to switch 105.

Anticoagulant contained in the satellite bag 21 commences to flow through the tube 30 into the bottom of the collection bag 22. Three seconds (or other desired interval) after the satellite hemostat 15 is opened, the light 123 signals the technician to open the donor hemostat 17. The technician manually opens the donor hemostat 17, thereby turning off the donor hemostat light 122 and starting the flow of blood through tube 35 into collection bag 22. The fluid entry nipples 32 and 36 in the bottom of collection bag 22 are located approximately $\frac{1}{8}$" apart and the flow of blood and anticoagulant into the bag 22 are intermingled upon entry. However, the blood only enters the bag 22 about three seconds after the anticoagulant flow is initiated so that the interior of the bag 22 is wetted before blood contact. As the blood and anticoagulant accumulate within the bag 22, its weight increases and it begins to descend. Such motion is permitted by longitudinal extension of the tape 25 which passes over pulleys 26 and 27 and the weight of the bag 22 is balanced by a tension force established in spring 28. The photocell detector 29 detects relative positions of the tape 25 during this time.

If after a nominal one-minute interval, at least 45 ml of blood have not flowed into the main collection bag 22, a "slow bleeder" flashing light 124 and audible alarm indicates to the technician that action is required. The technician can deactivate the audible signal by pressing the audible reset switch 126 while performing whatever other actions are required.

During a normal blood collection procedure (with no "slow bleeder" conditions), anticoagulant and blood continue to flow into the main collection bag 22 until about 450 ml of blood and anticoagulant are collected. This weight of fluid is detected by the longitudinal extension of spring 28, and as measured by the photocell detector 29 on the tape 25. At this point, the donor hemostat solenoid 101 is actuated closing the hemostat 17. This action also turns on a flashing "collection completed" light 125 and sounds an audible alarm. The electronic alarm can again be deactivated by pressing the audible reset switch 126.

The technician then removes the needle 37 from the donor and raises the covers of the hemostats 15 and 17. The tubes 30 and 35 are removed, the bags 21 and 22 are lifted from the hooks 23 and 24 respectively, and the technician performs the normal post-phlebotomy stripping and sealing actions.

In the event that the collection is not completed within ten minutes after the start and the "collection completed" signals have not been actuated, the donor hemostat 17 is closed automatically by the solenoid 101 by means of a timing mechanism (not shown), and the "slow bleeder" visual and aural signals are activated. This again alerts the technician to take action as required.

It is contemplated that the electronic circuitry required to provide the desired signals can take on a variety of forms so long as it meets the operational specifications described herein. It is also contemplated that the apparatus as shown and described herein can accommodate collection bags of different size and configuration, and will also be capable of accommodating collection bags currently under development. An example of such a bag is one in which anticoagulant is placed in a satellite bag during manufacture rather than within the main collection bag.

It is also contemplated that the "three second timer" which alerts the technician to open the donor hemostat 17 may be adjustable between an interval of 3-16 seconds in order to permit a greater flow of anticoagulant to wet the interior walls of the collection bag 22.

It is additionally contemplated that the apparatus can be calibrated to permit the collection of a predetermined quantity of blood in amounts ranging between 50 ml and 600 ml. Current practice is more or less standardized at 450 ml.

It is to be understood that the embodiment shown and described is the preferred one, and that many changes and modifications may be made without departing from the spirit of the invention. This invention is not to be considered as limited to the embodiment shown and described except insofar as the claims may be so limited.

We claim:

1. Apparatus for monitoring the collection of blood from a donor into a plastic bag assembly which includes a blood collection bag, an anticoagulant supply bag, a first pliable tube interconnecting the two bags and a second pliable tube connected at one end to the blood collection bag and carrying a needle on its free end for insertion into a vein of the donor and comprising:
   a horizontal base;
   an upright support column mounted on said base;
   a control console disposed in a horizontal plane and mounted on top of said column;
   a first relatively fixed support for mounting the anticoagulant supply bag beneath said console;
   a second extendable support for mounting the blood collection bag beneath said console and being movable downward proportionately to the weight of blood and anticoagulant collected;
   a first manually actuatable hemostat means adapted to receive and restrict the flow of anticoagulant through the first tube;
   a second manually and electromagnetically actuatable hemostat means adapted to receive and restrict the flow of blood through the second tube; and
   electrical means effective to actuate said second hemostat means according to prescribed blood collection procedures.

2. The apparatus of claim 1 including:
   a longitudinally extendable tape attached to said second support; and
   resilient means attached to said tape and mounted within said apparatus and adapted to allow longitudinal extension at said tape proportional to the weight of blood and anticoagulant received within the blood collection bag and thereby regulate the mixing of anticoagulant with the blood at a substantially constant ratio.

3. The apparatus of claim 2 including:
   detector means for measuring the longitudinal extension of said tape.

4. The apparatus of claim 1 including:
   second electrical timing means operable to provide a warning signal indicating that less than some prescribed amount of blood has been collected within a prescribed time interval.

5. The apparatus of claim 3 including:
   electrical indicating means actuated by said detector means for announcing the completion of a blood collection procedure.

6. The apparatus of claim 1 including:
   first electrical timing means effective to provide an alerting signal a few seconds after manually opening said first hemostat means.

* * * * *